United States Patent [19]

DeVale

[11] Patent Number: 5,464,391
[45] Date of Patent: Nov. 7, 1995

[54] IRRIGATION SYSTEM FOR A SURGICAL SITE

[75] Inventor: Donald P. DeVale, Bloomingdale, Ill.

[73] Assignee: Northgate Technologies Inc., Elgin, Ill.

[21] Appl. No.: 205,698

[22] Filed: Mar. 3, 1994

[51] Int. Cl.⁶ .................................................. A61M 31/00
[52] U.S. Cl. ........................... 604/67; 604/118; 604/123; 604/131; 604/151; 128/DIG. 12; 128/DIG. 13
[58] Field of Search .................................. 604/49, 51, 67, 604/82, 118, 123, 131, 151, 153; 128/DIG. 12, DIG. 13; 417/477 A, 423.1, 360, 43; 415/206

[56] References Cited

U.S. PATENT DOCUMENTS

| | | |
|---|---|---|
| 4,702,73 | 10/1987 | Wright et al. . |
| 3,508,546 | 4/1970 | Rogers et al. ............................ 604/151 |
| 3,900,022 | 8/1975 | Widran . |
| 4,180,074 | 12/1979 | Murry et al. . |
| 4,187,847 | 2/1980 | Loeser ............................... 128/DIG. 12 |
| 4,261,360 | 4/1981 | Perez . |
| 4,423,727 | 1/1984 | Widran et al. . |
| 4,604,089 | 8/1986 | Santangelo et al. . |
| 4,650,462 | 3/1987 | DeSatnick et al. . |
| 4,655,197 | 4/1987 | Atkinson . |
| 4,713,051 | 12/1987 | Steppe et al. . |
| 4,714,464 | 12/1987 | Newton . |
| 4,790,816 | 12/1988 | Sundblom et al. . |
| 4,795,424 | 1/1989 | Burner . |
| 4,798,580 | 1/1989 | DeMeo et al. . |
| 4,818,186 | 4/1989 | Pastrone et al. ......................... 604/153 |
| 4,820,265 | 4/1989 | DeSatnick et al. . |
| 4,838,856 | 6/1989 | Mulreany et al. ......................... 604/67 |
| 4,850,972 | 7/1989 | Schulman et al. ...................... 604/151 |
| 4,865,584 | 9/1989 | Epstein et al. ............................ 604/67 |
| 4,895,144 | 1/1990 | Cook et al. . |
| 4,900,302 | 2/1990 | Newton . |
| 4,940,457 | 7/1990 | Olson . |
| 4,963,131 | 10/1990 | Wortrich . |
| 5,019,038 | 5/1991 | Linden ..................................... 604/151 |
| 5,053,002 | 10/1991 | Barlow . |
| 5,098,387 | 3/1992 | Weist et al. . |
| 5,106,366 | 4/1992 | Steppe . |
| 5,152,746 | 10/1992 | Atkinson et al. . |
| 5,163,900 | 11/1992 | Wortrich . |
| 5,176,629 | 1/1993 | Kullas et al. . |
| 5,178,606 | 12/1993 | Ognier et al. . |
| 5,195,958 | 3/1993 | Phillips . |
| 5,246,422 | 9/1993 | Favre . |
| 5,261,883 | 11/1993 | Hood et al. . |
| 5,344,436 | 9/1994 | Fontenot et al. ......................... 607/104 |

FOREIGN PATENT DOCUMENTS 2378494  8/1978  France .

Primary Examiner—Corrine M. Maglione
Assistant Examiner—N. Kent Gring
Attorney, Agent, or Firm—Willian Brinks Hofer Gilson & Lione

[57] ABSTRACT

An irrigation system and method for providing fluid from a source of irrigating fluid to a surgical site, in particular a surgical site access to which is provided by a small incision or a natural orifice of the body. The irrigation system includes a control unit that is used with a cassette. The control unit includes a motor under the control of a controller, a sensor for sensing the flow of fluid in the cassette, a sensor for sensing pressure in the cassette, and a user control panel. The cassette includes a fluid flow passageway having an inlet connected to the source of irrigating fluid and an outlet for providing fluid to the surgical site. A pump located in the cassette is driven by the motor. The pump has limited efficiency when presented with back pressure to thereby limit to a safe level an amount of pressure that can be delivered to the surgical site. The system may be used to irrigate or distend a surgical site.

28 Claims, 3 Drawing Sheets

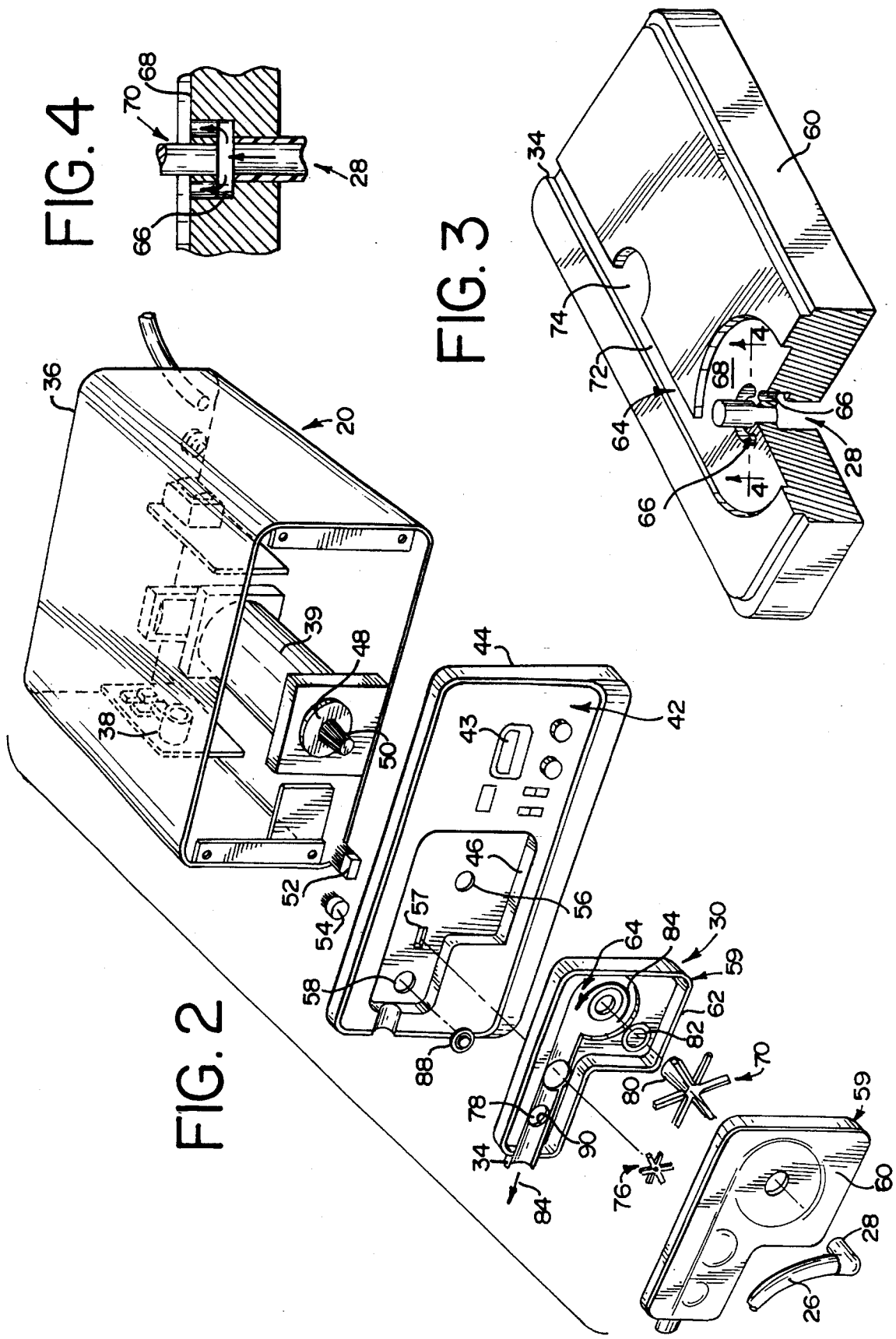

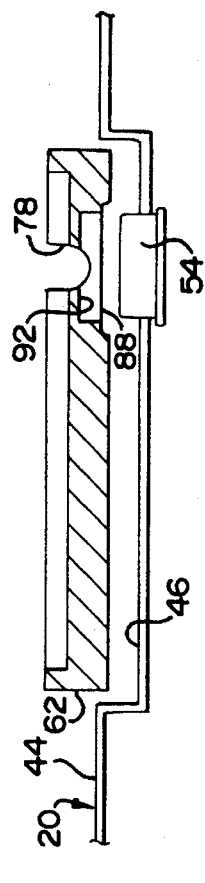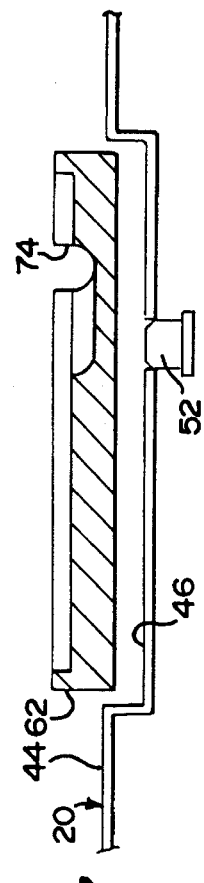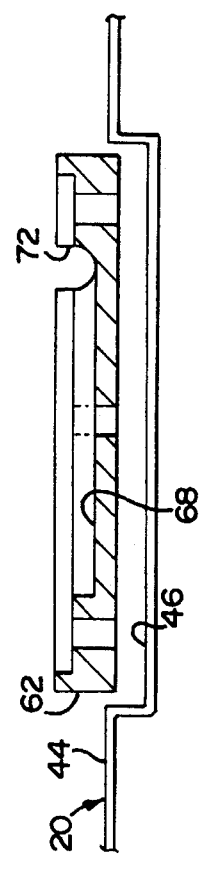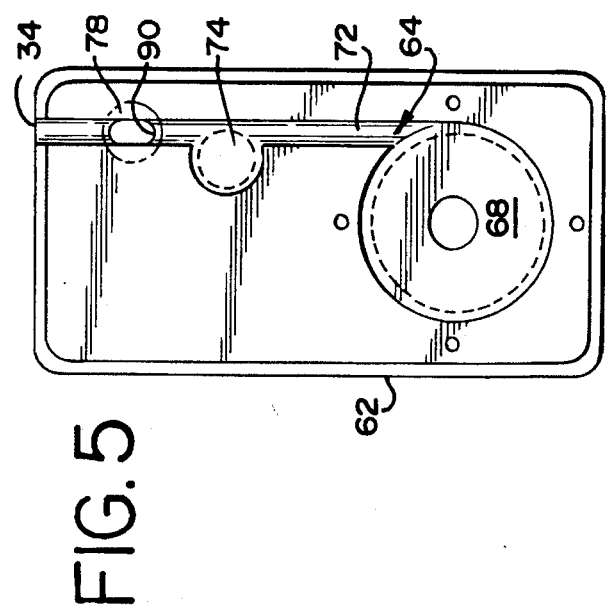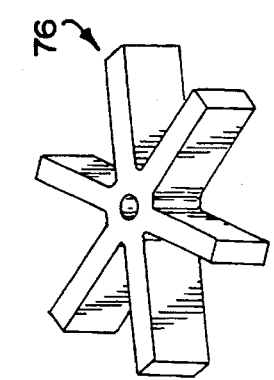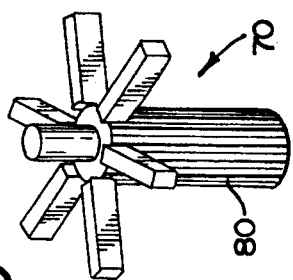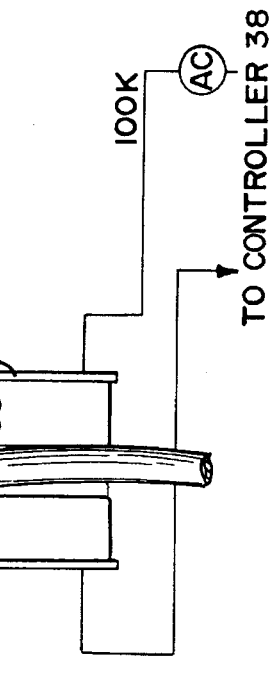

IRRIGATION SYSTEM FOR A SURGICAL SITE

BACKGROUND OF THE INVENTION

The present invention relates to a system for providing fluid to a body site and in particular the present invention relates to an irrigation/distension system and method for providing an irrigation fluid, such as saline, to a surgical site or organ that is accessed through a relatively small incision, natural orifice of the body, or in conjunction with a laparoscope, endoscope, resectoscope or similar device.

Certain surgical procedures, such as urological, gynecological, and laparoscopic surgeries, are performed inside the body either through an apparatus or a very small incision or through a small natural orifice of the body. An advantage of performing surgery in these ways is that it is less traumatic to the patient and allows quicker recovery, compared to conventional open surgery. When performing these types of surgeries, because the site of the surgical activity is inside the body, the surgical area must be observed remotely, such as by means of an optical fiber scope connected to an eyepiece or via a video monitor.

One difficulty with performing any surgical procedure is that blood or tissue may obstruct the surgical area. Even with conventional surgeries performed through a relatively large, open incision, it is routine to flush the surgical area with sterile water to clear the area to facilitate observation and to enable the physician to proceed. The usual procedure for providing irrigation for flushing of surgical sites consists of providing several plastic bags, e.g. two liter bags, containing sterile water, hanging the bags on an IV pole, connecting tubing to the bags, and letting the fluid flow to the surgical site by adjusting clamps on the tubing. Pressure for driving the fluid to the surgical site is provided by the difference in elevation between the surgical site and the water bags.

Blood or cut tissue can be especially a problem for surgeries performed through small incisions or natural orifices of the body. With surgeries performed this way, blood or cut tissue can obscure the viewing device used to observe the surgical area. Accordingly, it is essential to clear the surgical area to remove blood or cut tissue so that the surgical site can be clearly observed in order that the surgery can proceed.

For surgery performed through a small incision or natural orifice, sterile water may also be used to clear and/or distend the surgical site. However, certain additional considerations pertain when fluid is delivered to a surgery that is performed through a small incision or natural orifice. For example, it is important to be sure that too much pressure does not build up inside the body. Also, it may be important to know how much fluid has been delivered to the surgical site to be sure that fluid has not been accumulating inside the body.

The usual procedure for delivering irrigating fluid to a surgical site provides results that are less than ideal. For example, there is little control of the pressure applied to the surgical site. Also, the pressure that is available may be less than desired. Further, it can be difficult for medical personnel to lift the water bags to a sufficient height to hang them on the IV pole. Also, recording the amount of water used must be done manually.

There are water pump systems available to aid in this process. However, certain types of pumps used in these systems, such as positive displacement pumps, may have a potential disadvantage since pressure control failure could result in damage to the internal organs of the patient. Accordingly, systems that use these types of pumps may also provide safeguards that add to the complexity and expense of these systems.

Accordingly, there is a need for an irrigation system that is inexpensive to produce and use, that provides the physician with important information regarding the delivery of controlled amounts of irrigation fluid, and which is safe so that the pressure generated is not harmful to the patient.

SUMMARY OF THE INVENTION

To address the above concerns, an irrigation system has been invented that can provide a controlled delivery of irrigating fluid such as water to clear and/or distend a surgical area. The system is particularly directed for use with surgeries, such as urological, gynecological and laparoscopic surgeries, in which the surgical area is located within the body in an area accessed via a small incision or a natural orifice. The irrigation system includes a control unit that is used with a cassette. The control unit includes a motor under the control of a controller, a sensor for sensing the flow of fluid in the cassette, a sensor for sensing pressure in the cassette, and a user control panel. The cassette includes a fluid flow passageway having an inlet connected to the source of irrigating fluid and an outlet for providing fluid to the surgical site. A pump located in the cassette is driven by the motor. The pump preferably has limited efficiency when presented with back pressure to thereby limit to a safe level an amount of pressure that can be delivered to the surgical site. The irrigation system can deliver fluid for flushing a surgical site or for distending a body cavity.

BRIEF DESCRIPTION OF THE DRAWINGS

FIG. 2 is a perspective exploded view of the control unit and cassette depicted in the embodiment of FIG. 1.

FIG. 3 is a perspective view of the front half of the cassette depicted in FIG. 2.

FIG. 4 is a sectional view of taken along lines 4—4' of FIG. 3.

FIG. 5 is a plan view of the rear half of the cassette depicted in FIG. 2.

FIG. 6 is a sectional view taken along lines 6—6' of FIG. 5 shown in exploded view with part of the control unit of FIG. 1.

FIG. 7 is a sectional view taken along lines 7—7' of FIG. 5 shown in exploded view with part of the control unit of FIG. 1.

FIG. 8 is a sectional view taken along lines 8—8' of FIG. 5 shown in exploded view with part of the control unit of FIG. 1.

FIG. 9 is a perspective view of the impeller depicted in FIG. 2.

FIG. 10 is a perspective view of the flow meter paddle wheel depicted in FIG. 2.

FIG. 11 is a plan view of the fluid detection sensor shown in FIG. 1.

DESCRIPTION OF THE PREFERRED EMBODIMENTS

Figure 1:
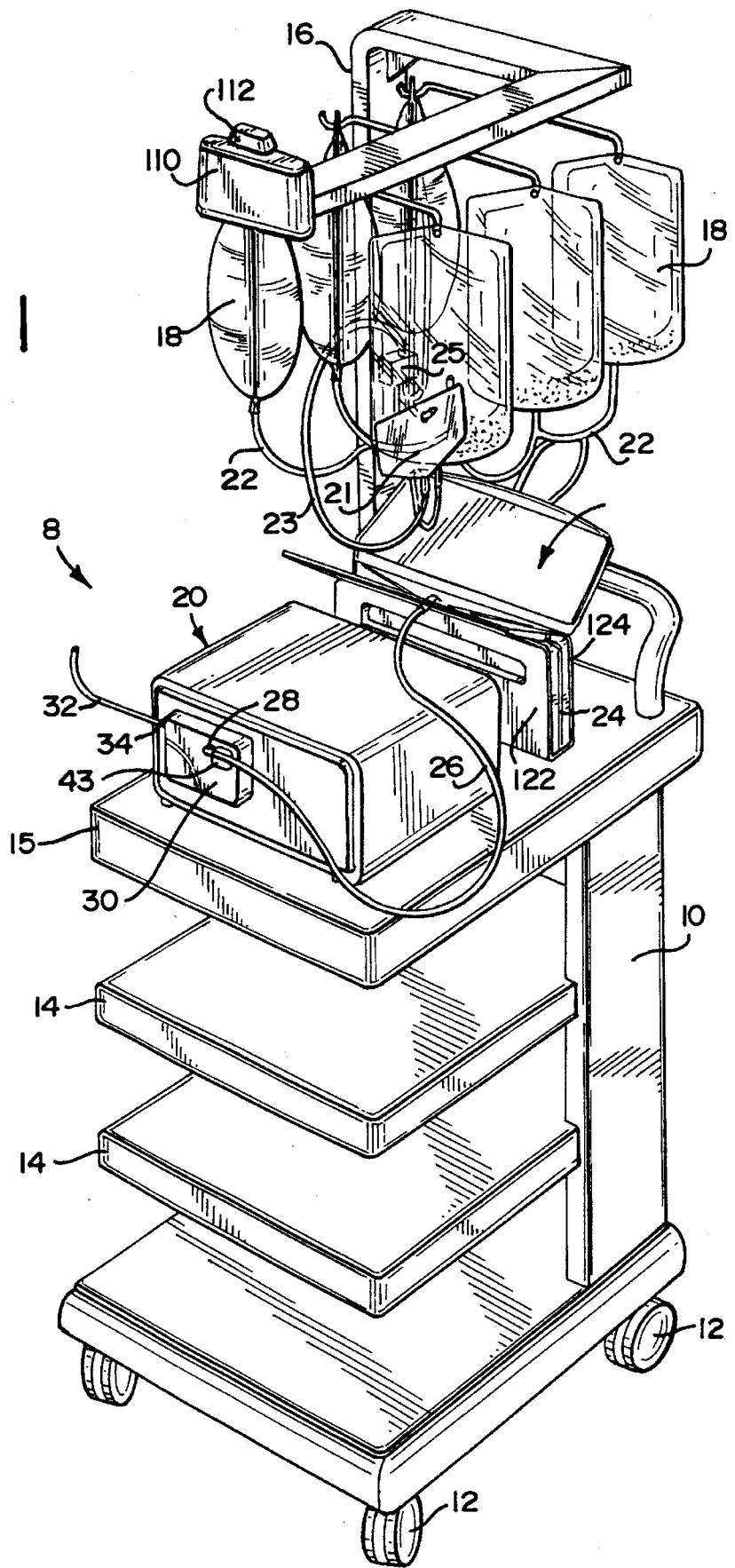
FIG. 1 is a perspective view of an irrigation system according to a first preferred embodiment of the present invention.

Referring to FIG. 1 there is shown a first preferred embodiment of the present invention. The embodiment shown in FIG. 1 is an irrigation system 8 that is used to provide an irrigating liquid, such as sterile water or saline, to a surgical site, and in particular to a surgical site, access to which is provided through a small surgical incision or natural orifice. Transurethral, gynecological and laparoscopic surgeries are examples of these type of surgeries.

The irrigation system 8 includes a cart 10 having wheels 12 and shelves 14 and 15. A pole 16 connects to the cart 10 and is used to suspend one or more bags 18 of an irrigation liquid, such two liter bags of sterile water or saline. A control unit 20 is located on one of the shelves 15. The additional shelves 14 may be used for storage of additional bags of fluid or other equipment. Each of the bags 18 connects to a manifold 21 via individual sections 22 of tubing. The manifold 21 includes a plurality of input ports corresponding to the number of bags 18 that can be used. The manifold 21 also includes an output port that connects via a tubing 23 to a reservoir 24. The tubing 23 leading to the reservoir 24 passes through a water detection sensor 25 which is connected to the control unit 20 to provide an output indicating whether the bags 18 have emptied, as explained below. In a preferred embodiment, the reservoir 24 is temperature-controlled to bring the fluid from the bags 18 to a desired temperature prior to use. The reservoir 24 also acts as a buffer to maintain fluid during changeover of the bags.

The fluid output from the reservoir 24 is attached via tubing 26 to an inlet 28 of a cassette 30. The cassette 30 is mounted on the control unit 20. Another section of tubing 32 connects to an outlet 34 of the cassette 30. The tubing 32 conveys irrigating fluid from the cassette 30 to the surgical site (not shown). The tubing 32 may be inserted directly into the surgical site, or alternatively, the tubing may connect to a surgical instrument that is used to provide access to the surgical site, such as a resectoscope (not shown). The cart 10 allows the fluid source 18, the control unit 20, and the cassette 30 to be located in a surgical operating room out of the way of the medical personnel yet conveniently close at hand so that the flow and pressure of the irrigating fluid to the patient can be readily controlled and monitored.

Referring to FIG. 2, there is an exploded view of the control unit 20 and cassette 30. The control unit 20 includes a housing 36 inside of which are located a controller 38 and a pump motor 39. User controls and displays 42 are located on a front panel 44 of the control unit housing 36. The user input controls and displays 42 provide for adjusting the flow and pressure of the irrigating fluid delivered to the surgical site. Also, the user input controls 42 may provide for establishing maximum or minimum limits for pressure and/or flow, or alternatively, limits may be pre-established and stored in a memory of the controller 38. The user control panel 42 may also provide a display 43 for indicating the total quantity of fluid provided during a surgical procedure, the pressure of the fluid being delivered, a graphical representation of the fluid pressure, etc.

The controller 38 is connected to the user input controls 42 and to the motor 39 in order that the motor 39 can be operated in accordance with the desired input from the user, as explained below. The pump motor 39 is a brushless, DC 1/16 horsepower rotary motor that is operated and controlled in speed by the controller 38. The controller 38 preferably includes two microprocessors and suitable memory for operation of the system and motor. In a preferred embodiment, the microprocessors may be conventional microprocessors, such as a model PIC16C57 for control of the motor and an 8031 for system control, however other models of microprocessors could also be used.

The front panel 44 of the control unit housing 36 also includes an area 46 for mounting the cassette 30. Extending through the front panel 44 in this area 46 is an output shaft 48 of the motor 39. Connection between the motor 39 and the cassette 30 is by a slotted or ribbed portion 50 of the output shaft 48. Also located in this area 46 are first and second sensors 52 and 54, for sensing flow rate and pressure, respectively, of the fluid in the cassette 30. The sensors 52 and 54 are connected to the controller 38. The output shaft 48 of the motor 39 and the first and second sensors 52 and 54 cooperate with the cassette 30 through apertures 56, 57, and 58 in the front panel 44 of the control unit 20.

As mentioned above, the cassette 30 mounts in the control unit 20 and specifically in the area 46 in the front panel 44. The cassette 30 includes a housing 59 composed of front and rear halves 60 and 62 that are bonded together by a suitable adhesive or other suitable means such as welding and so on. In a preferred embodiment, the cassette housing 59 is made of a suitable plastic material, such as polypropelene, although other materials may also be acceptable. The housing 59 has a length of approximately 6 inches, a height of approximately 3.125 inches, and a thickness of approximately 1 inch.

These front and rear halves 60 and 62 of the cassette housing 59 define an internal cavity or flow passage way 64 between the inlet 28 and the outlet 34. The flow passage way 64 includes several segments. As mentioned above, the inlet 28 connects to the source of sterile water 18. Referring to FIG. 4, the flow passage way 64 includes a first or inlet segment 66 which extends from the inlet 28 to a circular shaped segment 68. In a preferred embodiment, the first segment 66 is formed of three arcuate shaped flow passages that extend through the front half 60 of the cassette housing 59.

An impeller 70 is located in the circular shaped segment 68 of the fluid passage way 64. Extending from the circular shaped segment 68 is a linear segment 72. Located along the linear segment 72 is another, smaller circular segment 74 that houses a flow meter paddle wheel 76. Located further downstream along the linear segment 72 is a pressure sensing area 78. The linear segment 72 terminates at the outlet 34.

The impeller 70 is mounted in the cassette housing 59 so that it can be driven by the output shaft 48 of the motor 39. Accordingly, the impeller 70 has a shape that engages or mates with the motor output shaft 50. Referring to FIG. 9, the impeller 70 preferably includes a base 80 that mates or engages with the output shaft 50 of the motor 39. Also, as shown in FIG. 9, the impeller 70 includes from 2 to 6 or more blades. In a preferred embodiment, the impeller 70 is made of a suitably durable material such as Teflon® or polypropelene.

Referring again to FIG. 2, an O-ring 82 or other suitable means are provided around the base 80 of the impeller 70 to provide a fluid tight seal between the impeller 70 and the housing 59 while allowing the impeller 70 to be rotatably driven by the motor 39. The impeller 70 rotates in the housing 59 so that it causes the fluid that enters the passage way 64 at the inlet 28 to be driven in the direction of the arrow 84 toward the outlet 34.

The first sensor 52, which is used to measure flow, is located so that it corresponds to the location of the flow meter paddle wheel 76. Flow of fluid through the passage way 64 causes the paddle wheel 76 to rotate. Rotation of the paddle wheel 76 is observed optically by the first sensor 52 that provides an output to the controller 38. A conversion routine in the controller calculates the flow rate based upon the rotational rate of the paddle wheel. Referring to FIG. 10, the paddle wheel 76 includes six blades and is made of a suitable material such as polypropelene.

Referring again to FIG. 2, in a preferred embodiment, the first sensor 52 is an infrared optic sensor. The infrared optic sensor 52 is located immediately adjacent to the paddle wheel 76 and detects the rotation of the paddles in order to determine the flow rate of the water being supplied to the patient. In order to facilitate optical observation of the paddle wheel movement, it is preferred that one side of the paddle wheel 76 is mirrored (or alternatively blackened), in order to provide as much contrast as possible. Also, in order to enable the first sensor 52 in the control unit 20 to observe the movement of the paddle wheel 76 located in the cassette 30, it is preferable that the wall of the cassette adjacent the paddle wheel 76 is translucent or transparent. In a preferred embodiment, the entire cassette housing 59 is transparent. Although it is preferred that the first sensor 52 is an optical sensor, other types of sensors could also be used, such as Hall effect type sensors.

As mentioned, located in the passage way 64 downstream of the paddle wheel 72 is a pressure sensing area 78. The second sensor 54, which is used to measure pressure, is located so that it corresponds to the location of the pressure sensing area 78. A portion of the wall of the housing 59 in the pressure sensing area 78 is formed of a flexible membrane 88. In a preferred embodiment, the flexible membrane is made of silicon rubber. In a preferred embodiment, the flexible membrane 88 located across an aperture 90 through a wall of the cassette housing 59. The flexible membrane 88 is directly adjacent the second sensor 54 which in a preferred embodiment is a pressure transducer. The aperture 90 is approximately ¾ inch in diameter and the flexible membrane 88 is bonded to the rear half 62 of the cassette housing 59 by a press-fit, an adhesive or other suitable bonding method. The aperture 90 is located along a lower portion of the wall defining the passageway 72 (when mounted) to reduce the effect of entrained air bubbles on the pressure sensing. To further reduce the effect of any air bubbles, when the cassette 30 is mounted in the control unit 20, the linear segment 72 is inclined slightly from the horizontal. For example, in a present embodiment the linear segment 72 is inclined by approximately 1 degree so that the outlet 34 of linear segment 72 is slightly higher than its upstream end at the segment 68. This inclination facilitates removal of air bubbles that might be entrained in the fluid and which might affect the pressure sensing measurement.

As shown in the exploded sectional view of FIG. 8, the flexible membrane 88 is mounted over a bored out section 92 of the housing half 62. The bored out section 92 is sized to receive the pressure sensor 54 which extends slightly out from the surface of the area 46 of the control unit front panel 44. Therefore, when the cassette 30 is mounted in the area 46 of the control unit 30, the membrane 88 is stretched tight against the pressure sensor 54 to ensure that pressure in the passage way 64 readily passes across the membrane 88 and is sensed by the sensor 54. The pressure of the fluid in the pressure sensing area 78 of the flow passage 64 causes a force to bear on the pressure transducer 54 directly through the flexible membrane 88. The pressure transducer 54 provides an output to the controller 38. As in the case of the flow sensor 52, an appropriate conversion routine in the controller calculates the pressure based upon the output of the transducer 54.

After fluid has passed the pressure sensing area 78, it exits the cassette 30 via the outlet 34. The fluid is then conveyed by tubing 32 to the surgical site.

Referring again to FIG. 1, the fluid detection sensor 25 provides an output that indicates whether the bags 18 have emptied. The fluid detection sensor 25 is located in the fluid path between the bags 18 and the reservoir 24, and preferably at the tubing 23 connecting the manifold 21 to the reservoir 24. In a preferred embodiment, the fluid detection sensor 25 is designed so that it avoids direct contact with the fluid to avoid possible contamination. In a preferred embodiment, the fluid detection sensor 25 utilizes capacitive sensing to determine the presence of fluid in the tubing 23. The tubing 23 passes through a slot 98 between two conductive plates 100 and 102. The plates 100 and 102 are spaced from each other forming a capacitor with the tubing 23 forming part of the dielectric material between them. Additional insulative material 104 may be also located between the plates 100 and 102. Coaxial cabling connects to the two plates and an AC current (e.g. 100K) is applied across them. Because the dielectric constant of a fluid, such as water, is significantly greater than that of air, an output signal taken off the capacitor plates provides a clear indication when fluid is no longer located in the tubing 23 and air occupies the tubing instead. The AC signal for driving the capacitors is provided by the control unit 20 and the output of the capacitors is also sent to control unit 20 so that the fluid detection sensor information can be conveyed to the medical personnel.

In a preferred embodiment, the fluid detection information is conveyed to the medical personnel via a secondary display 110. The secondary display 110 is connected to the control unit 20 and is located in a conspicuous location such as at an end of the pole 16. The secondary display 110 includes an empty bag warning indicator 112. The empty bag indicator 112 may be a blinking light or an audible alarm. The secondary display 110 may additionally include some of the same information included on the display 43, such as the pressure of delivered fluid, the volume of fluid already delivered, and the elapsed time of the procedure.

As also mentioned above, the reservoir 24 is temperature-controlled. Again referring to FIG. 1, the reservoir 24 is located between a pair of heat conductive plates 122 and 124. A heating element connects to the plates 122 and 124 to provide heat to the fluid passing through the reservoir 24. In a preferred embodiment, the heating element consists of one or more power resistors driven by a low voltage (e.g. 24 v DC) signal. The power resistors and conductive plates raise the temperature of the fluid so that it is approximately at the body temperature of the patient, when delivered.

To operate the irrigation system 8, a physician or other medical personnel use the control panel 42 or a remote controller to control the flow rate of the irrigating fluid supplied to the surgical site by setting a desired flow rate or pressure level. If the flow rate is chosen as a controlling parameter, the controller 38 compares the desired flow rate with the actual flow rate as measured by the flow sensor 52. If the actual flow rate is not at the desired flow rate, the controller 38 outputs a signal to the motor 39 to adjust the motor speed until the desired flow rate is achieved. In a similar manner, the physician can also control the pressure at which the fluid is being applied. If the pressure is chosen as a controlling parameter, the controller 38 compares the desired pressure with the actual pressure as measured by the pressure sensor 54. The controller 38, operating in conjunction with the pressure sensor 54, can be used to establish an upper pressure limit to assure that the pressure does not exceed a safe limit in the body. In addition, the total quantity of fluid can be determined at any time during the procedure and displayed to the physician.

It is a significant advantage of the preferred embodiment of the present invention that a pumping means, such as an impeller, is used that is incapable of producing too high a pressure in the flow passage 64. A pump apparatus, such as an impeller, has reduced efficiency when presented with back pressure. This limits to a safe level the maximum amount of pressure that the irrigation system can deliver to the surgical site. By contrast, other prior systems that use other types of pumps, such as positive displacement type pumps including peristaltic pumps, must provide additional safeguards to ensure that too high a pressure is not created inside the body. According to a preferred embodiment of the present invention, the pressure produced in the body will not exceed a predetermined safe limit regardless of how fast the motor rotates the impeller. Once the pressure reaches a certain limit, the fluid will tend to leak around the impeller blades. In one embodiment, the impeller is incapable of imparting a pressure greater than about 4 psi. In order to provide this level of safety, the impeller 70 may be designed to have a relatively loose fit in the area 68 of the flow passageway 64. In a preferred embodiment, there is a small clearance on the order of approximately ⅛ inch between the blades of the impeller 70 and the walls of the housing halves 60 and 62 that define the area 68 of the passage way in which the impeller is located. In this manner, the cassette 30 provides an inherent, self-limiting safety feature in addition to any safeguards provided by the controller 38. If a different maximum pressure is desired, the cassette can be provided with an impeller having a smaller clearance between the impeller blades and the walls of the housing halves. For example, in an embodiment in which a maximum pressure of 9 psi is desired, the impeller can be designed with a blade clearance of only 1/16 inches. Because all the rest of the parts of the cassette can be made the same, cassettes for different procedures with corresponding different maximum pressure outputs can be readily manufactured by substitution of impellers of slightly different sizes. Of course, appropriate indicia indicating the maximum pressure output can be provided on the outside face of the cassette.

One of the important considerations addressed by the irrigation system described above is to provide for control of irrigation fluid flow and pressure in a system at a reasonable cost. In a preferred embodiment, the system disclosed above provides these advantages because the reusable portions of the system are isolated from the disposable portion. Specifically, the cassette 30 provides an interface between the irrigating fluid and the control unit 20 including the motor 39 so that control of the pressure and flow rate of the irrigating fluid can be provided without the irrigating fluid coming into contact with the motor 39, the controller 38, or any of the sensors, such as sensors 52 and 54. Because irrigating fluid comes in contact only with the cassette, the cassette may be made to be disposable. The control unit 20, since it does not physically come in contact with the irrigating fluid, can be reused. The cooperative arrangement provided by the cassette 30 and the reusable control unit 20 provides a relatively high degree of control, safety and convenience in an irrigation system that is economical and efficient to use since disposable components are relatively inexpensive.

Although it is presently preferred to provide the cassette as a disposable item, in another version it may be disassembled, sterilized, and reused.

It is another advantage of the embodiment described above that multiple fluid bags can be attached together and the fluid delivered to a surgical site. In addition, when the warning alarm 112 signals that the initial group of bags has become emptied, a new group of bags can be attached to the manifold 21 without interrupting the delivery of fluid to the surgical site. This feature is provided because the reservoir 24 contains enough fluid so that a new supply of fluid bags can be connected to the manifold after the alarm 112 indicates an empty condition but before the reservoir 24 empties.

It is intended that the foregoing detailed description be regarded as illustrative rather than limiting and that it is understood that the following claims including all equivalents are intended to define the scope of the invention.

I claim:

1. An irrigation system for providing fluid from a source of irrigating fluid to a surgical site comprising a control unit cooperatively associated with a cassette, and in which the control unit comprises:

a controller;

a motor under the control of said controller;

a first sensor for sensing the flow of fluid in said cassette, said first sensor operatively connected to the controller;

a second sensor for sensing pressure in the cassette, said second sensor operatively connected to the controller; and user input controls operatively connected to the controller;

and in which the cassette comprises:

a housing defining a chamber, said chamber having an inlet connected to said source of irrigating fluid and an outlet for providing fluid to the surgical site; and an impeller located in said housing and driven by said motor.

2. The system of claim 1 in which the cassette further comprises:

a flowmeter located in said chamber downstream of said impeller, said flowmeter providing an output to said first sensor.

3. The system of claim 1 in which the cassette further comprises:

a flexible panel located in said housing downstream of said impeller, said flexible panel providing an output to said second sensor.

4. The system of claim 1 in which said cassette is disposable.

5. The system of claim 1 in which said control unit is isolated from the irrigating fluid.

6. The system of claim 1 in which said cassette is reusable.

7. A system for providing irrigation fluid from a source to a surgical site through a small incision or a natural orifice of the body, the system comprising:

a control unit having a microprocessor and a motor under the control of said microprocessor and user input controls operatively connected to the microprocessor;

a cassette mountable on said control unit, said cassette comprising:

a housing defining a flow passageway, said flow passageway having an inlet for connection to said source of fluid and an outlet for providing fluid to the surgical site; and a pump located in said housing and driven by said motor, said pump having reduced efficiency when presented with back pressure to thereby limit to a safe level an amount of pressure that can be delivered to the surgical site; and a first sensor for sensing the flow of fluid in said passageway downstream from said pump, said first sensor providing an output to said microprocessor.

8. The system of claim 7 further comprising:
a paddle wheel located in said passageway adjacent to said first sensor.

9. The system of claim 7 further comprising:
a second sensor for sensing pressure in said passageway downstream from said pump, said second sensor providing an output to said microprocessor.

10. The system of claim 9 further comprising:
a flexible panel located in said housing adjacent to said second sensor.

11. The system of claim 7 in which said pump comprises an impeller located in said flow passageway.

12. The system of claim 7 further comprising:
a fluid sensor for sensing the presence of fluid, said sensor located on at least one of said control unit and said cassette and operable to output a signal indicative of a lack of fluid whereby said source of fluid may be replenished.

13. An irrigation system for providing fluid from a source to a surgical site in the body through a small incision or natural orifice, the system comprising:
a disposable cassette having a fluid flow passage therethrough with an input on an upstream side for connection to the source and an output on a downstream side for providing fluid to the surgical site;
an impeller located in said fluid flow passage;
a reusable control unit upon which said disposable cassette can be mounted, said control unit having:
a motor having an output shaft to which said impeller can be engaged;
a first sensor for sensing fluid speed in said fluid flow passage downstream of said impeller;
a second sensor for sensing pressure in said fluid flow passage downstream of said impeller; and
a controller connected to said motor, said first sensor, and said second sensor adapted to control delivery of fluid to the surgical site from the source of fluid based upon input by an operator and input from the sensors.

14. The system of claim 13 further comprising:
a fluid sensor for sensing the presence of fluid, said fluid sensor located on at least one of said control unit and said cassette and operable to output a signal indicative of a lack of fluid whereby said source of fluid may be replenished.

15. A disposable cassette for use with a control unit for providing fluid from a source of irrigation fluid to a surgical site, said disposable cassette comprising:
a housing releasably mountable to said control unit, said housing having an input from the source of irrigation fluid and an output to the surgical site, said housing defining a fluid flow passage between the input and the output;
a pump located in said housing and driven by said motor, said pump having limited efficiency when presented with back pressure to thereby limit to a safe level an amount of pressure that the pump can deliver to the surgical site; and
a flow indicator operatively associated with said fluid flow passage downstream of said pump, said flow indicator providing an output to said control unit,
whereby an actual flow rate of fluid downstream of said pump toward the surgical site can be determined.

16. The system of claim 15 in which said pump comprises an impeller located in said flow passageway.

17. A disposable cassette for use with a control unit for providing fluid from a source of irrigation fluid to a surgical site, said disposable cassette comprising:
a housing releasably mountable to said control unit, said housing having an input and an output to the surgical site, and further in which said housing defines a fluid flow passage between the input and the output to the surgical site;
an impeller located in said fluid flow passage, said impeller being driven by a motor in said control unit; and
a flow indicator operatively associated with said fluid flow passage downstream of said impeller, said flow indicator providing an output to said control unit, whereby an actual flow rate of fluid downstream of said impeller toward said surgical site can be determined.

18. The cassette of claim 17 in which said flow indicator comprises a paddle wheel mounted in said fluid flow passage.

19. A disposable cassette for use with a control unit for providing fluid from a source of irrigation fluid to a surgical site, said disposable cassette comprising:
a housing releasably mountable to said control unit, said housing having an input from the source of irrigation fluid and an output to the surgical site and defining a fluid flow passage between the input and the output;
an impeller located in said fluid flow passage, said impeller being driven by a motor in said control unit;
a pressure sensitive area associated with said fluid flow passage downstream of said impeller, said pressure sensitive area providing an output to said control unit, whereby a measure of pressure of fluid downstream of said impeller toward said surgical site can be determined.

20. The cassette of claim 19 in which said pressure sensitive area comprises:
a pressure sensitive panel located in a wall of said cassette downstream of said impeller.

21. A method of irrigating a surgical site, comprising the steps of:
mounting a disposable cassette on a control unit;
attaching a source of irrigation fluid to an input of the cassette;
delivering fluid to the surgical site from an output of the cassette;
operating an impeller located in a passageway of the cassette by means of a motor located in the control unit;
sensing pressure and flow in the cassette downstream from said impeller; and
adjusting the operation of the motor and thereby the impeller based upon the pressure and flow sensed.

22. The method of claim 21 further comprising the step of:
accessing the surgical site through a small incision.

23. The method of claim 21 further comprising the step of:
displaying information indicating a total amount of fluid delivered.

24. The method of claim 21 further comprising the step of:
providing an alarm when the source of fluid needs to be replenished.

25. The method of claim 24 further comprising the step of:
attaching an additional source of fluid to said cassette after an initial source is emptied without interrupting the delivery of fluid to the site.

26. The method of claim 21 in which the step of attaching a source of irrigation fluid further comprises the step of:
attaching multiple bags of fluid to a manifold so that fluid from the multiple bags is delivered to the surgical site.

27. A method of irrigating a surgical site, comprising the steps of:

mounting a disposable cassette on a control unit;

attaching a source of irrigation fluid to an input of the cassette;

delivering fluid to the surgical site from an output of the cassette;

operating an impeller located in a passageway of the cassette by means of a motor located in the control unit;

sensing pressure in the cassette downstream from said impeller; and adjusting the operation of the motor and thereby the impeller based upon the pressure sensed.

28. The method of claim 27 further comprising the step of:

sensing flow in the cassette downstream from said impeller.

* * * * *

UNITED STATES PATENT AND TRADEMARK OFFICE
CERTIFICATE OF CORRECTION

PATENT NO. : 5,464,391
DATED : November 7, 1995
INVENTOR(S) : Donald P. DeVale

It is certified that error appears in the above-indentified patent and that said Letters Patent is hereby corrected as shown below:

<u>On the Title Page</u>: Item [56]

In column 1, line 1 under "References Cited U.S. PATENT DOCUMENTS", delete "4,702,73" and substitute --4,702,733--.

Signed and Sealed this

Twenty-sixth Day of May, 1998

Attest:

BRUCE LEHMAN

*Attesting Officer*    *Commissioner of Patents and Trademarks*